US012055533B1

(12) United States Patent
Li et al.

(10) Patent No.: US 12,055,533 B1
(45) Date of Patent: Aug. 6, 2024

(54) MONITORING DEVICES FOR METHANE GAS IN HOT THAW LAKE PONDS IN TUNDRA REGIONS

(71) Applicant: NORTHWEST INSTITUTE OF ECO-ENVIRONMENT AND RESOURCES, CAS, Gansu (CN)

(72) Inventors: Guoyu Li, Lanzhou (CN); Buxiang Wang, Lanzhou (CN); Dun Chen, Lanzhou (CN); Qingsong Du, Lanzhou (CN)

(73) Assignee: NORTHWEST INSTITUTE OF ECO-ENVIRONMENT AND RESOURCES, CAS, Lanzhou (CN)

( * ) Notice: Subject to any disclaimer, the term of this patent is extended or adjusted under 35 U.S.C. 154(b) by 0 days.

(21) Appl. No.: 18/644,069

(22) Filed: Apr. 23, 2024

(30) Foreign Application Priority Data

Jun. 25, 2023 (CN) .......................... 202310747594.1

(51) Int. Cl.
*G01N 33/18* (2006.01)
(52) U.S. Cl.
CPC ..... *G01N 33/1886* (2013.01); *G01N 33/1826* (2013.01)
(58) Field of Classification Search
CPC . G01N 33/18; G01N 33/1826; G01N 33/1886
See application file for complete search history.

(56) References Cited

FOREIGN PATENT DOCUMENTS

| CN | 102313673 A | | 1/2012 | |
|---|---|---|---|---|
| CN | 103282769 A | * | 9/2013 | ........... G01N 1/2273 |
| CN | 110173268 A | | 8/2019 | |
| CN | 111910669 A | | 11/2020 | |

(Continued)

OTHER PUBLICATIONS

Machine translation of CN 103282769 A (Year: 2013).*

(Continued)

*Primary Examiner* — Nathaniel J Kolb
(74) *Attorney, Agent, or Firm* — METIS IP LLC

(57) ABSTRACT

A monitoring device for methane gas in a hot thaw lake pond in a tundra region is provided, comprising a top plate, an adjusting mechanism, and a monitoring mechanism. A bottom portion of the top plate is fixedly connected with a fixed column, and the fixed column is slidably mounted on the adjusting mechanism. The monitoring mechanism is connected to the adjusting mechanism, and the monitoring mechanism controls entry and exit of water to be detected and detect a methane gas in the water. The position of the mounting cylinder of the monitoring mechanism is adjusted by an electric push rod to facilitate the monitoring of methane concentration at different positions. In the mounting cylinder of the monitoring mechanism, a turntable with a filter membrane that is lifted and rotated is provided to facilitate controlling the direction of liquid movement while promoting the upward movement of the gas to detect methane concentration, and the liquid periodically to detect the methane concentration, which achieves the purpose of detecting the methane concentration by periodic liquid (Continued)

replacement. Additionally, the present disclosure also provides a debris removal mechanism that is capable of scraping weeds from the outside of the mounting cylinder.

10 Claims, 10 Drawing Sheets

(56) References Cited

FOREIGN PATENT DOCUMENTS

| | | | | |
|---|---|---|---|---|
| CN | 113655192 A | * | 11/2021 | |
| CN | 115524458 A | | 12/2022 | |
| JP | 6564980 B1 | * | 8/2019 | ........... E02B 15/104 |
| JP | 6564980 B1 | | 8/2019 | |
| WO | WO-2016157121 A1 | * | 10/2016 | ............. B63G 8/001 |

OTHER PUBLICATIONS

Machine Translation of CN 113655192 (Year: 2021).*
Machine translation of JP 6564980 B1 (Year: 2019).*
Decision to Grant a Patent in Chinese Application No. 202310747594.1 mailed on Jul. 28, 2023, 5 pages.

* cited by examiner

MONITORING DEVICES FOR METHANE GAS IN HOT THAW LAKE PONDS IN TUNDRA REGIONS

CROSS-REFERENCE TO RELATED APPLICATIONS

The application claims priority to Chinese Patent Application No. 202310747594.1, filed on Jun. 25, 2023, the entire contents of which are incorporated herein by reference.

TECHNICAL FIELD

The present disclosure relates to the field of gas monitoring technology, and in particular, to monitoring devices for methane gas in a hot thaw lake pond in a tundra region.

BACKGROUND

The permafrost is also known as tundra, permafrost, or tundra. In physical geography, permafrost refers to an environment in which trees cannot grow due to low temperatures and a short growing season. In geology, permafrost refers to a variety of rocks and soils that are below 0° ° C. and contain ice. The permafrost under a condition that the ground has been below the freezing point of water for more than a thousand, or even tens of thousands of years is called continuous permafrost. The area of perennial permafrost, seasonal permafrost, and short-term tundra regions on the earth accounts for about 50% of the land area, with perennial permafrost accounting for 25% of the land area. Disruption of the thermal balance of perennial permafrost due to self-heating stresses and anthropogenic damage causes depressions in the earth's surface. Thus, a thermally thawed subsidence is generated, or a hot thaw lake pond is generated when the depression has standing water. Wetland plants may emit methane as they grow. Methane is the second most important greenhouse gas to nitrogen dioxide and has a significant impact on global warming.

For the currently used monitoring device for methane gas in a hot thaw lake pond in a tundra region, when moves gradually downwardly in the hot thaw lake pond, impurities or weeds are prone to adhere to its surface, which affects the amount of liquid that enters the monitoring device. Furthermore, it is difficult for the monitoring device to monitor methane concentration in different locations when monitoring methane gas.

SUMMARY

Objective of the present disclosure is to solve the above technical problems, one or more embodiments of the present disclosure provide a monitoring device for methane gas in a hot thaw lake pond in a tundra region, comprising a top plate, an adjusting mechanism, and a monitoring mechanism. A bottom portion of the top plate is fixedly connected with a fixed column, the fixed column is slidably mounted on the adjusting mechanism, and the adjusting mechanism move up and down along the fixed column to adjust a fixed position of the adjusting mechanism. The monitoring mechanism is connected to the adjusting mechanism, and the monitoring mechanism controls entry and exit of water to be detected and detect a methane gas in the water. The monitoring mechanism includes a second lateral electric push rod, a slide seat, a second vertical electric push rod, a mounting cylinder, and a sealing base plate. The slide seat is slidably mounted in a lateral chute of the adjusting mechanism, and the slide seat is connected with an action end of the second lateral electric push rod. A top end of the second vertical electric push rod is fixed to the slide seat, and the mounting cylinder is fixedly connected to a bottom end of the second vertical electric push rod. A motor box, a first electric telescopic rod, a turntable, a second electric telescopic rod, and a methane detection sensor are provided in the mounting cylinder. The motor box is fixed on a top of the mounting cylinder, a motor is provided in the motor box, an output shaft of the motor is connected with the first electric telescopic rod, an action end of the first electric telescopic rod is connected to the turntable, and the turntable is slidably mounted in the mounting cylinder. The first electric telescopic rod drives the turntable to slide up and down along the mounting cylinder, the motor drives the turntable to rotate through the first electric telescopic rod, the turntable has a plurality of stirring heads on a bottom plane of the turntable, and the turntable is provided with a nanofiltration membrane. The second electric telescopic rod is connected to a bottom portion of the turntable, an action end of the second electric telescopic rod is connected to the sealing base plate to drive the sealing base plate to move up and down to realize opening and closing of the sealing base plate and a lower port of the mounting cylinder. A debris removal mechanism is provided on the monitoring mechanism, the debris removal mechanism includes a rotation ring rotationally sheathed to the mounting cylinder, and snap rings are provided on upper and lower sides of the rotation ring. The rotation ring is connected to the sealing base plate by a telescopic connecting plate, a cleaning plate are connected to the rotation ring, a cutting edge is provided on an outer wall of the cleaning plate, and curved guide plates are provided on both sides of the cleaning plate.

In some embodiments, the adjusting mechanism includes an articulating ring, the articulating ring is slidably sheathed to the fixed column, a support arm is fixedly connected to an outer wall of the articulating ring, and the support arm is configured to mount the monitoring mechanism. A baying post is provided on the articulating ring along a radial direction of the articulating ring, and a plurality of baying holes is provided on the fixed column. Adjustment and positioning of the articulating ring along an up and down position of the fixed column is realized by adjusting the baying post to fit different baying holes.

In some embodiments, a base is fixedly connected to a bottom portion of the fixed column.

In some embodiments, an air supply mechanism is provided at the bottom portion of the top plate, and the air supply mechanism includes a first lateral electric push rod, a slider, a first vertical electric telescopic rod, an air supply box, a first air outlet pipe, and a second air outlet pipe. The slider is slidably mounted in a slide groove of the top plate, and the slider is connected to an action end of the first lateral electric push rod. A top of the first vertical electric telescopic rod is fixedly connected to the slider, an action end of the first vertical electric telescopic rod is connected to the air supply box, and the first air outlet pipe and the second air outlet pipe is connected to an air outlet of the air supply box. The first air outlet pipe is a vertical pipe for delivering air to the monitoring mechanism, and the second air outlet pipe is a curved pipe for delivering air to an outer surface of the fixed column.

In some embodiments, the cleaning plate is provided downward and inclined outwardly.

In some embodiments, a gap between each position on each of the curved guide plates that is passed through in sequence and a wall of the mounting cylinder is progressively decreasing from a side of each of the curved guide plates connected to the cleaning plate to another side of each of the curved guide plates.

In some embodiments, a motorized cutting device is provided at a bottom end of the cleaning plate.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, wherein.

DETAILED DESCRIPTION

Figure 1:
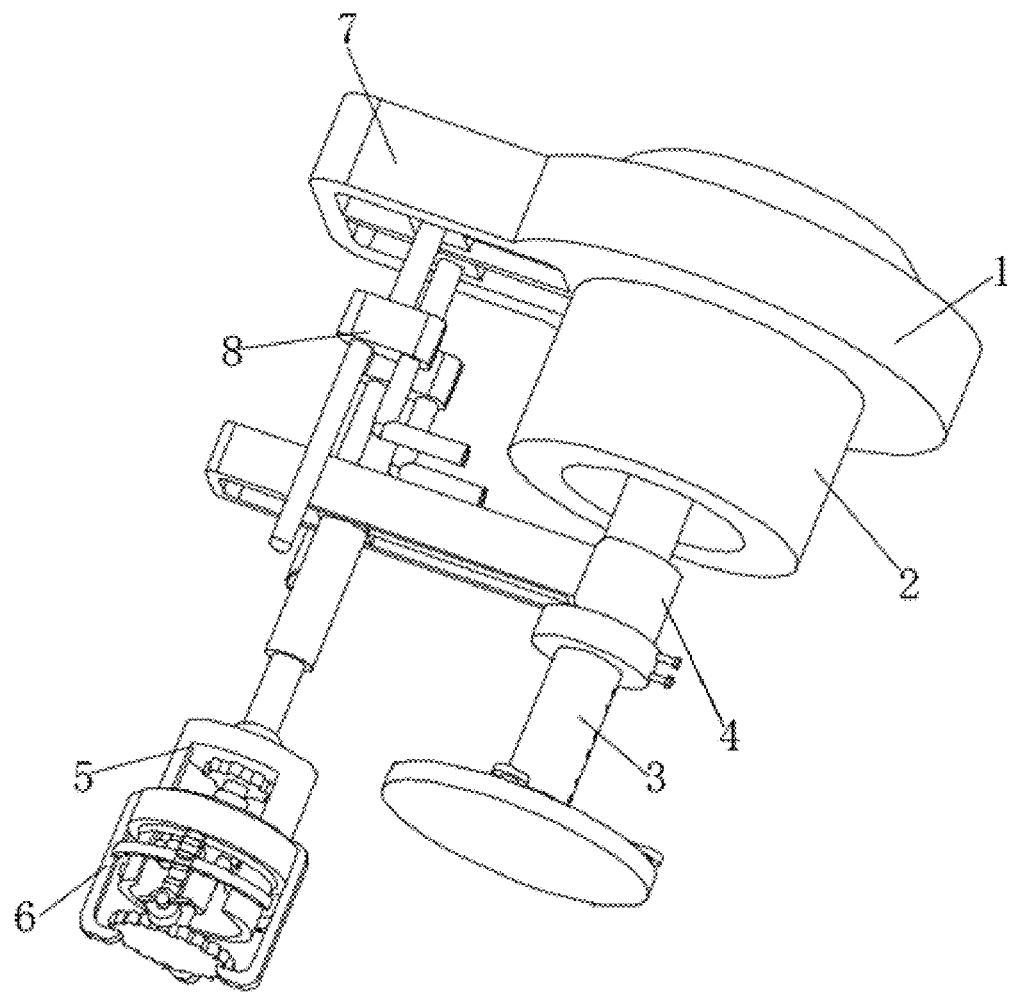
FIG. 1 is a schematic diagram illustrating a structure of a monitoring device for methane gas in a hot thaw lake pond in a tundra region according to some embodiments of the present disclosure.

In order to more clearly illustrate the technical solutions of the embodiments of the present disclosure, the accompanying drawings required to be used in the description of the embodiments are briefly described below. Obviously, the accompanying drawings in the following description are only some examples or embodiments of the present disclosure, and it is possible for a person of ordinary skill in the art to apply the present disclosure to other similar scenarios in accordance with the accompanying drawings without creative labor. The present disclosure may be applied to other similar scenarios based on these drawings without creative labor. Unless obviously obtained from the context or the context illustrates otherwise, the same numeral in the drawings refers to the same structure or operation.

It should be understood that as used herein, the terms "system", "device", "unit" and/or "module" as used herein is a way to distinguish between different components, elements, parts, sections or assemblies at different levels. However, the words may be replaced by other expressions if other words accomplish the same purpose.

As shown in the present disclosure and the claims, unless the context clearly suggests an exception, the words "one," "a", "an", and/or "the" do not refer specifically to the singular, but may also include the plural. Generally, the terms "including" and "comprising" suggest only the inclusion of clearly identified steps and elements. In general, the terms "include" and "comprise" only suggest the inclusion of explicitly identified steps and elements that do not constitute an exclusive list, and the method or device may also contain other elements.

The present disclosure is described in further detail below in connection with the accompanying drawings and specific embodiments. The embodiments of the present disclosure are given for the purpose of exemplifying and describing, and are not intended to be omission-free or to limit the present disclosure to the disclosed form. Many of the modifications and variations will be apparent to one of ordinary skill in the art. Examples of embodiments have been selected and described to better illustrate the principles and practical applications of the present disclosure and to enable those of ordinary skill in the art to understand the present disclosure and thereby devise a variety of embodiments with a variety of modifications suitable for a particular use. embodiments suitable for a particular application.

Figure 2:
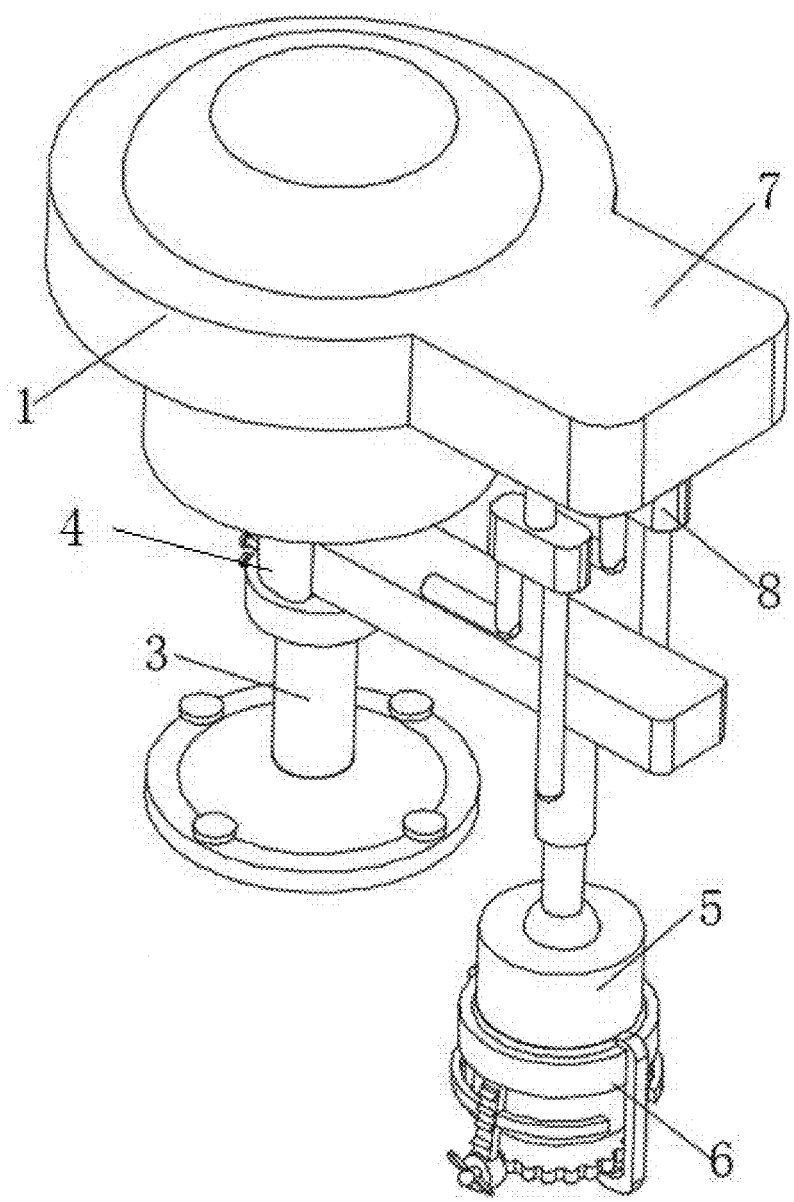
FIG. 2 is a schematic diagram illustrating a side structure of a monitoring device for methane gas in a hot thaw lake pond in a tundra region according to some embodiments of the present disclosure.
Figure 3:
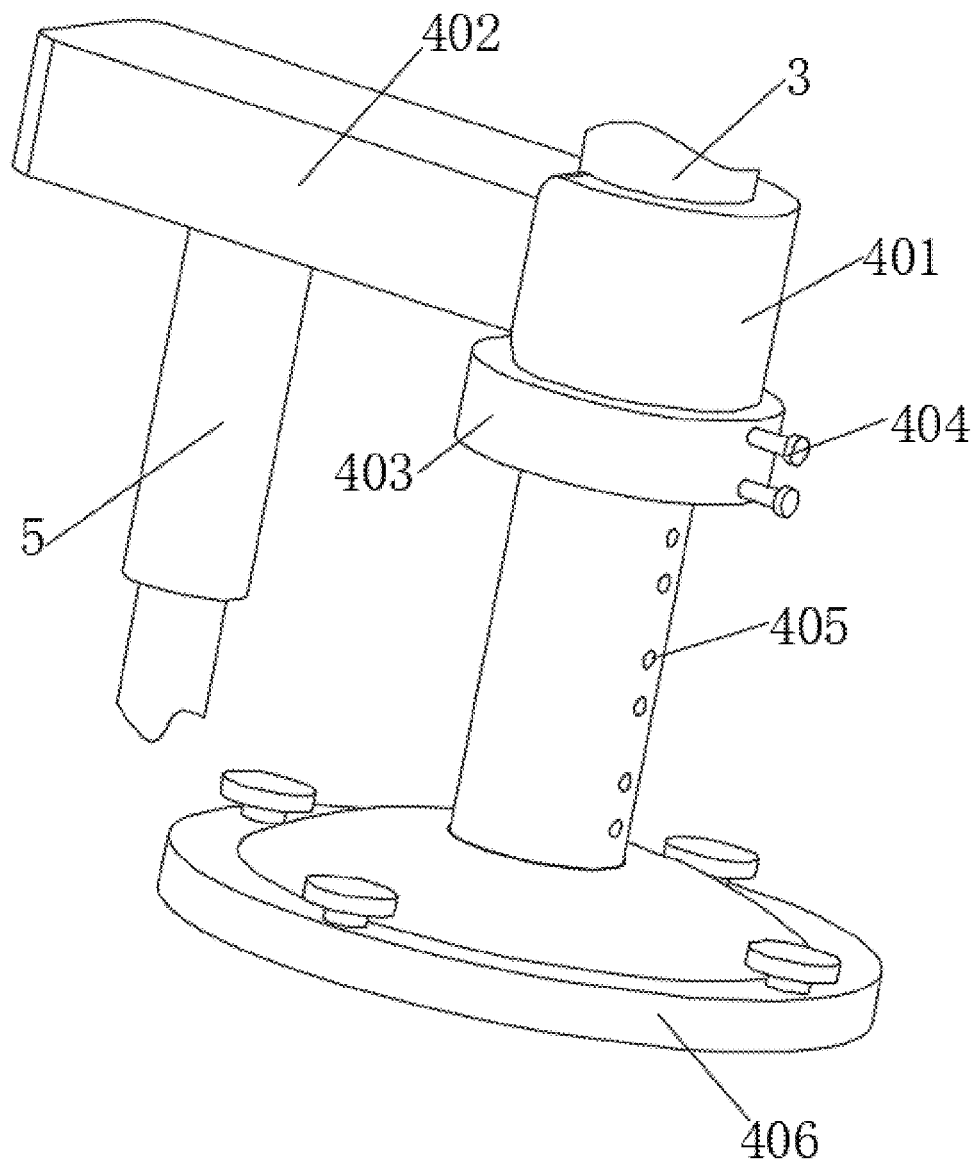
FIG. 3 is a schematic diagram illustrating a structure of an adjusting mechanism according to some embodiments of the present disclosure.

FIG. 1 is a schematic diagram illustrating a structure of a monitoring device for methane gas in a hot thaw lake pond in a tundra region according to some embodiments of the present disclosure. FIG. 2 is a schematic diagram illustrating a side structure of a monitoring device for methane gas in a hot thaw lake pond in a tundra region according to some embodiments of the present disclosure. FIG. 3 is a schematic diagram illustrating a structure of an adjusting mechanism according to some embodiments of the present disclosure.

As shown in FIG. 1-FIG. 2, the present disclosure provides the monitoring device for methane gas in the hot thaw lake pond in the tundra region (referred to as a monitoring device hereinafter) including a top plate 1, an adjusting mechanism 4, a monitoring mechanism 5, a debris removal mechanism 6, and an air supply mechanism 8.

A bottom portion of the top plate 1 is fixedly connected with a fixed ring 2, the fixed ring 2 is coaxially fixedly connected with a fixed column 3, and the fixed column 3 is slidingly mounted with an adjusting mechanism 4 that is capable of moving up and down along the fixed column 3 to adjust a fixed position thereof.

The adjusting mechanism 4 may be configured to manually adjust an initial position of the monitoring mechanism 5 and to strengthen the fixing of the monitoring device. As shown in FIG. 3, the adjusting mechanism 4 includes an articulating ring 401, the articulating ring 401 is slidably sheathed to the fixed column 3, and a support arm 402 is fixedly connected to an outer wall of the articulating ring 401. The support arm 402 may be configured to mount the monitoring mechanism 5.

A bottom ring 403 is connected to a bottom portion of the articulating ring 401, the bottom ring 403 is provided with a baying post 404 along a radial direction of the bottom ring 403, and a plurality of baying holes 405 are provided on the fixed column 3. Adjustment and positioning of a height position of the articulating ring 401 along the fixed column 3 may be achieved by adjusting the baying post 404 with different baying holes 405.

In some embodiments of the present disclosure, the monitoring device may be fixed as a whole at a bottom portion of the monitoring device by setting up the adjusting mechanism, and then an initial height and a lowest position of the monitoring mechanism may be adjusted by manually adjusting the adjusting mechanism, so as to achieve the purpose of facilitating control of the initial position of the monitoring mechanism and strengthening the fixing of the monitoring device.

In some embodiments, a base 406 may be fixedly connected to a bottom portion of the fixed column 3. The adjusting mechanism 4 may have the advantage of facilitating the adjustment of the initial position of the monitoring mechanism 5 and enhancing the fixing of the monitoring device. Depending on a monitored height, the baying post 404 may be manually disassembled and a suitable height may be selected to manually move the position of the bottom ring 403 on the fixed column 3, and then clamp the baying post 404 to the inside of the bottom ring 403 and the baying hole 405. Through the above operation, the height of the articulating ring 401 may be determined, so that the articulating ring 401 may drive the support arm 402 to move up and down to adjust the height of the monitoring mechanism 5.

An articulating plate 7 may be fixedly connected to a side portion of the top plate 1, and the air supply mechanism 8 may be provided on a bottom portion of the articulating plate 7.

The air supply mechanism 8 may supply air to the monitoring mechanism 5 and the fixed column 3 that are exposed to the air, preventing dust accumulation.

Figure 8:
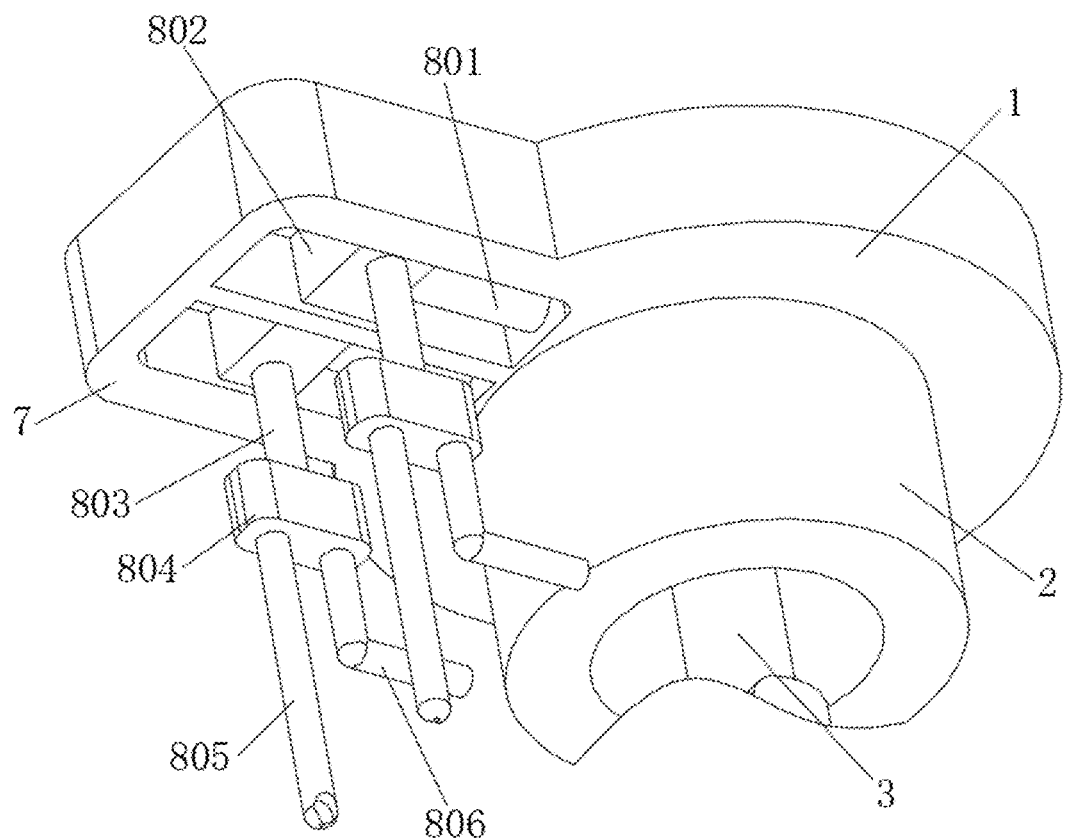
FIG. 8 is a schematic diagram illustrating a structure of an air supply mechanism according to some embodiments of the present disclosure.

FIG. 8 is a schematic diagram illustrating a structure of an air supply mechanism according to some embodiments of the present disclosure.

As shown in FIG. 8, the air supply mechanism 8 includes a first lateral electric push rod 801, a slider 802, a first vertical electric telescopic rod 803, an air supply box 804, a first air outlet pipe 805 and a second air outlet pipe 806. The slider 802 is slidably mounted in a slide groove on a bottom surface of the articulating plate 7, and the slider 802 is connected to an action end of the first lateral electric push rod 801, and the slider 802 is driven to slide laterally by the first lateral electric push rod 801.

In some embodiments, a top of the first vertical electric telescopic rod 803 may be fixedly connected to the slider 802, the action end of the first vertical electric telescopic rod 803 may be connected to the air supply box 804, and the air supply box 804 may be provided with a blower inside the air supply box 804, which is capable of producing an airflow. The first air outlet pipe 805 and the second air outlet pipe 806 may be connected to an air outlet of the air supply box 804. The first air outlet pipe 805 refers to a vertical pipe for delivering air to the monitoring mechanism 5. The second air outlet pipe 806 refers to a curved pipe for delivering air to an outer surface of the fixed column 3, preventing dust from accumulating to make it difficult for the adjusting mechanism 4 to adjust. When working, through the first lateral electric push rod 801 and the first vertical electric telescopic rod 803, the position of the air supply box 804 may be adjusted, and the positions of the air outlet of the first air outlet pipe and the second air outlet pipe may be further adjusted.

In some embodiments of the present disclosure, providing the air supply mechanism may facilitate delivering air to the monitoring mechanism and the fixed column, to prevent dust accumulation due to the fact that the two are exposed to the outside of the device, which makes it difficult to regulate the device, and to achieve the purpose of facilitating delivering air to the exposed adjustment position to prevent dust accumulation.

Figure 4:
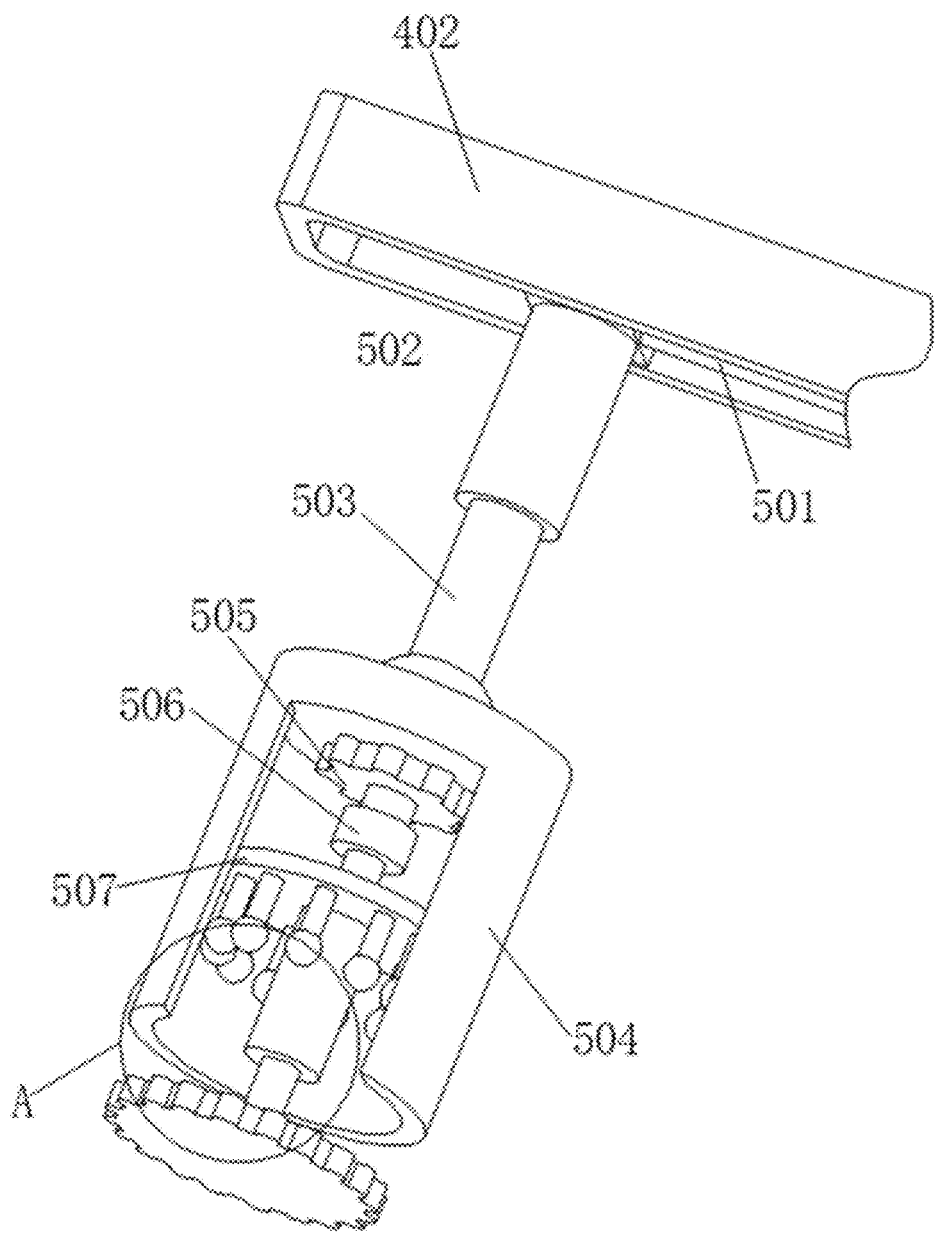
FIG. 4 is a schematic diagram illustrating a structure of a monitoring mechanism according to some embodiments of the present disclosure.
Figure 5:
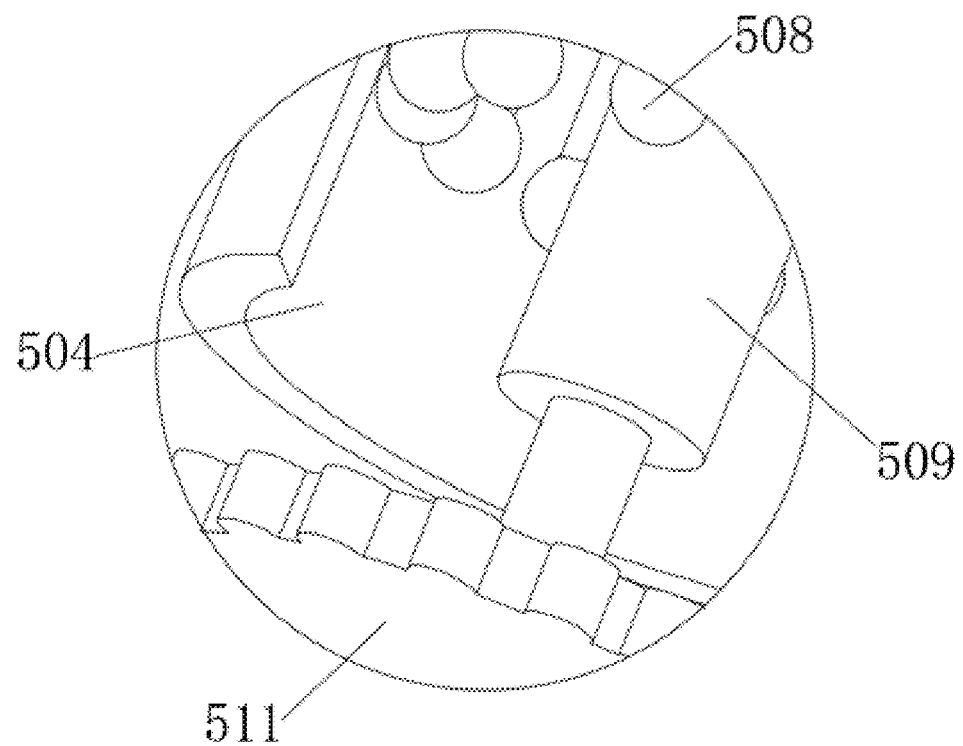
FIG. 5 is a schematic diagram illustrating a partially enlarged region at position A in FIG. 4 according to some embodiments of the present disclosure.

FIG. 4 is a schematic diagram illustrating a structure of a monitoring mechanism according to some embodiments of the present disclosure. FIG. 5 is a schematic diagram illustrating a partially enlarged region at position A in FIG. 4 according to some embodiments of the present disclosure.

The monitoring mechanism 5 may control entry and exit of water to be detected and detects a methane gas in the water. Referring to FIG. 4-FIG. 5, the monitoring mechanism 5 includes a second lateral electric push rod 501, a slide seat 502, a second vertical electric push rod 503, a mounting cylinder 504, and a sealing base plate 511. The slide seat 502 is slidably mounted in a lateral chute on a bottom surface of the support arm 402 of the adjusting mechanism 4, the slide seat 502 is connected to an action end of the second lateral electric push rod 501, and the slide seat 502 may be driven to slide transversely by the second lateral electric push rod 501.

A top end of the second vertical electric push rod 503 is fixed to the slide seat 502, and the mounting cylinder 504 is fixedly connected to a bottom end of the second vertical electric push rod 503. The mounting cylinder 504 is a cylinder structure with an opening provided on the bottom. Inside of the mounting cylinder 504 are provided with a motor box 505, a first electric telescopic rod 506, a turntable 507, a second electric telescopic rod 509, and a methane detection sensor. The methane detection sensor is preferably provided at a top of the mounting cylinder 504. The motor box 505 is fixed at a top center of the mounting cylinder 504. The motor box 505 is provided with a motor, an output shaft of which is connected to the first electric telescopic rod 506. The first electric telescopic rod 506 is coaxially provided with the mounting cylinder 504, and an action end of the first electric telescopic rod 506 is connected to the turntable 507.

The turntable 507 is slidably mounted in the mounting cylinder 504, the first electric telescopic rod 506 is capable of driving the turntable 507 to slide up and down along the mounting cylinder 504, and the motor is capable of rotating the turntable 507 through the first electric telescopic rod 506. A plurality of the stirring heads 508 are provided on a bottom surface of the turntable 507, and the turntable 507 synchronously drives the stirring heads 508 to rotate when the turntable 507 rotates. There is a sliding sealing fit between the turntable and an inner wall of the mounting cylinder 504, and the turntable is also provided with a nanofiltration membrane. The second electric telescopic rod 509 is connected to the bottom portion of the turntable 507, and the action end of the second electric telescopic rod 509 is connected to the sealing base plate 511, which is capable of driving the sealing base plate 511 to move up and down to realize opening and closing of the sealing base plate 511 and a lower port of the mounting cylinder 504.

When the monitoring mechanism 5 is in use, the mounting cylinder 504 is adjusted to a specified monitoring position by adjusting the second lateral electric push rod 501 and the second vertical electric push rod 503, after arriving at a specified monitoring position, the second electric telescopic rod inside the mounting cylinder 504 is activated to drive the sealing base plate 511 to move downwardly, and the lower port of the mounting cylinder 504 is opened, so that liquid gradually enters into the mounting cylinder 504. The second electric telescopic rod 509 is then controlled to contract, driving the sealing base plate 511 to move upwardly to close the lower port of the mounting cylinder 504. Then the motor in the motor box 505 is activated to drive the turntable 507 to rotate, and the turntable 507 drives the stirring head 508 at the bottom thereof to rotate, accelerating the separation of the gases in the water to be detected, and the gases pass through the nanofiltration membrane on the turntable and moves upward, which in turn detects methane concentration in the gas through the methane detection sensor.

It should be noted that, since the sealing base plate 511 is driven to rotate when the turntable 507 rotates, when the lower port of the mounting cylinder 504 is closed, there is a sliding gap fit between the sealing base plate 511 and the lower port of the mounting cylinder 504. The sealing base plate 511 may effectively prevent the exchange between an external water and the water to be detected that has already entered the mounting cylinder 504.

At the end of the monitoring, the monitoring mechanism 5 controls the first electric telescopic rod 506 to extend and drive the turntable 507 to move downwardly to the lower port of the mounting cylinder 504 to discharge the water. Subsequently, the mounting cylinder may be adjusted to different positions by adjusting the second lateral electric push rod 501 and the second vertical electric push rod 503, then repeating the above-described detecting actions, so that the methane concentration in the water at different positions may be monitored. At the end of the monitoring, the second vertical electric push rod 503 is contracted, the mounting cylinder 504 is raised to the water surface, and then the air supply mechanism 8 is periodically turned on to blow air to the monitoring mechanism 5 and the fixed column 3.

In some embodiments of the present disclosure, by setting up the monitoring mechanism, the position of the mounting cylinder can be controlled by controlling the travel of the second lateral electric push rod and the second vertical electric push rod according to a test location, facilitating monitoring the methane concentration at different positions. Furthermore, in the mounting cylinder, providing the turntable with a filter membrane that may be lifted and rotated facilitates controlling the movement direction of the liquid, and at the same time, promotes upward movement of the gas to detect the methane concentration, which facilitates monitoring the methane concentration by periodic liquid replacement.

Figure 6:
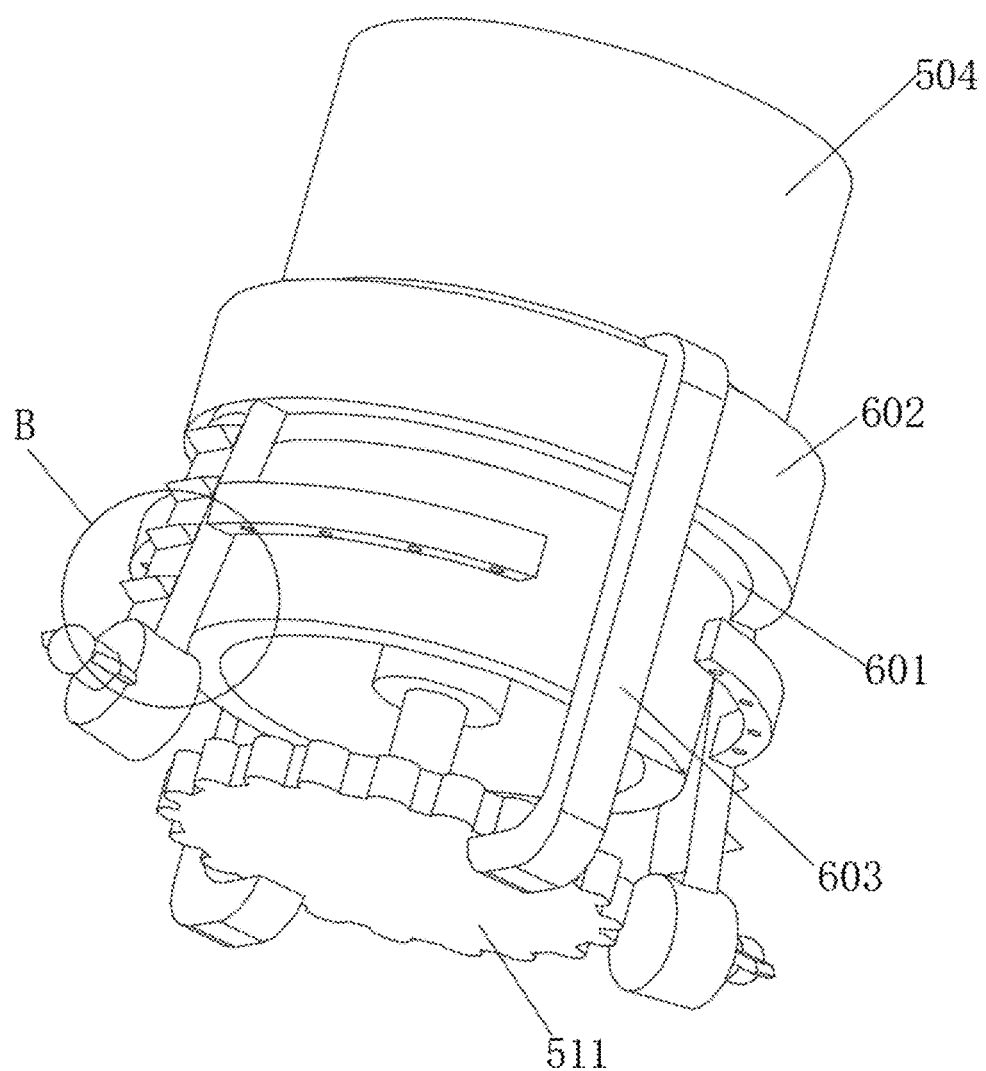
FIG. 6 is a schematic diagram illustrating a structure of a debris removal mechanism according to some embodiments of the present disclosure.
Figure 7:
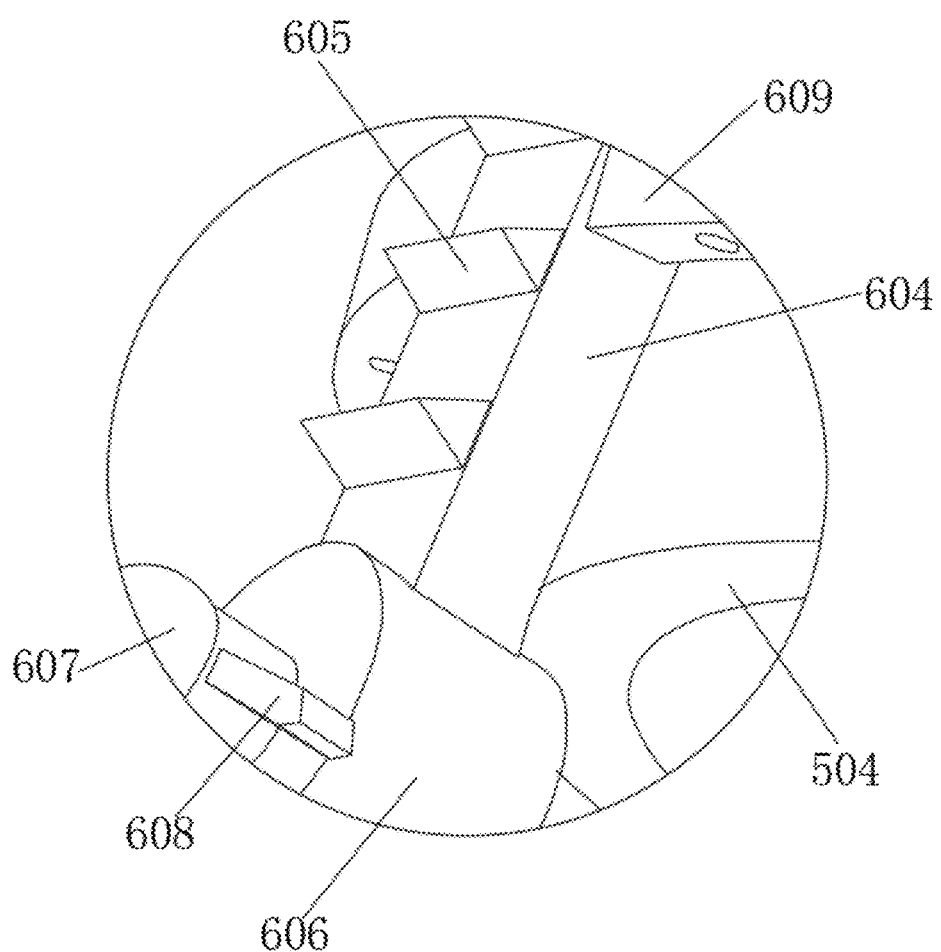
FIG. 7 is a schematic diagram illustrating a partially enlarged region at position B in FIG. 6 according to some embodiments of the present disclosure.

FIG. 6 is a schematic diagram illustrating a structure of a debris removal mechanism according to some embodiments of the present disclosure. FIG. 7 is a schematic diagram illustrating a partially enlarged region at position B in FIG. 6 according to some embodiments of the present disclosure.

The debris removal mechanism 6 is configured to scrape weeds or impurities in the lake and pond outside the monitoring mechanism 5. Referring to FIG. 6-FIG. 7, the debris removal mechanism 6 includes a rotation ring 602. The rotation ring 602 is rotatably sheathed to the mounting cylinder 504, and snap rings 601 are provided on upper and lower sides of the rotation ring 602 to limit an axial movement of the rotation ring 602. The rotation ring 602 is connected to the sealing base plate 511 through the telescopic connecting plate 603, and the sealing base plate 511 rotates synchronously with the rotation of the rotation ring 602. As the length of the telescopic connecting plate 603 may be varied, the rotation ring 602 does not affect the up and down movement of the sealing base plate 511.

A cleaning plate 604 is connected to a wall of the rotation ring 602, the cleaning plate 604 is preferably disposed facing downward and inclined outward, a plurality of protruding cutting edges 605 are provided at equal intervals on an outer wall of the cleaning plate 604, and curved guide plates 609 are provided on both sides of the cleaning plate 604. From a side of the curved guide plates 609 connected to the cleaning plate 604 to another side of the curved guide plates 609, a gap between each position on the curved guide plates that is passed in sequence, and a wall of the mounting cylinder 504 is gradually decreasing. In this way, when the sealing base plate 511 drives the rotation ring 602 to rotate, the cleaning plate 604 rotates with the rotation ring 602, the curved guide plate 609 can effectively prop up the weeds in the surroundings during the rotation of the cleaning plate 604, and the cutting edge 605 on the cleaning plate 604 is utilized to cut the weeds.

In some embodiments, a motorized cutting device may also be provided at a bottom end of the cleaning plate 604 to improve the effect of removing weeds. The motorized cutting device may include a drive motor 606, a rotary head 607 mounted to the drive motor 606, and a knife 608 mounted to the rotary head 607.

In some embodiments of the present disclosure, by providing the debris removal mechanism, when the mounting cylinder is gradually moving downwardly in a hot thaw lake pond, impurities or weeds are prone to attach the outside of the mounting cylinder, which affects the amount of liquid that enters into the mounting cylinder. Therefore, by controlling the monitoring mechanism, the debris removal mechanism may be driven to rotate to remove external debris. In such a case, the purpose of scraping weeds or impurities on the outside of the mounting cylinder is achieved.

When the monitoring device shown in FIG. 1 monitors methane concentration in the hot thaw lake pond in a tundra region, the articulating plate 7 and the air supply mechanism 8 of the monitoring device shown in FIG. 1 are located above the water surface, a bottom portion of the fixed column 3 on a right side of the top plate 1 of the monitoring device shown in FIG. 1 is fixed to a riverside of the hot thaw lake pond, the monitoring mechanism 5 and the debris removal mechanism 6 on a left side of the top plate 1 of the monitoring device as shown in FIG. 1 are deepened into the water, and the water to be detected in the hot thaw lake pond is obtained and monitored, so as to obtain the methane concentration of the hot thaw lake pond in the tundra region. When the monitoring device finishes monitoring, the monitoring mechanism 5 and the debris removal mechanism 6 are raised out of the water surface by the motor, and the air supply mechanism blows air to the fixed column 3 and the monitoring mechanism 5 that are exposed to the air to avoid dust accumulation.

In some embodiments, the monitoring device may further include a communication module and a controller. The communication module is configured to send monitoring data obtained by the monitoring device to a remote terminal and to receive a control command sent by the remote terminal. The controller is configured to control a regulating lever based on the control command transmitted by the communication module. The communication module and the controller are disposed on the top plate 1, and the communication module is electrically connected to the motor of the regulating lever. The communication module and the controller are electrically connected, and the communication module and the remote terminal are wirelessly connected.

In some embodiments, the regulating lever may include at least one of the first lateral electric push rod 801, the first vertical electric telescopic rod 803, the second lateral electric push rod 501, the second vertical electric push rod 503, the first electric telescopic rod 506, and the second electric telescopic rod 509. In some embodiments, a motor of the regulating lever may include a motor that controls movement of the regulating lever and a motor that controls rotation of the regulating lever.

In some embodiments, the monitoring device may also include an underwater ranging sensor and an underwater camera device (e.g., an underwater video camera). The underwater ranging sensor and the underwater camera device may be disposed on the exterior of the mounting cylinder 504 and/or on the debris removal mechanism 6.

In some embodiments, the monitoring data may include methane concentration data and/or environmental data. The methane concentration data refers to data that relates to the methane concentration in a monitoring region, e.g., the methane concentration data in the monitoring region (e.g., the hot thaw lake pond).

The environmental data refers to data that relates to the environment of the watershed being monitored by the monitoring device. In some embodiments, the environmental data may include a depth sequence 910-2, a width sequence 910-3, and an image data sequence.

The depth sequence 910-2 refers to a sequence consisting of depths of the water bottom corresponding to a plurality of different horizontal position points of the monitoring device in the monitoring waters.

The width sequence 910-3 refers to a sequence consisting of horizontally moveable distances corresponding to a plurality of position points of the monitoring device with different water depths in the monitoring waters.

Figure 10:
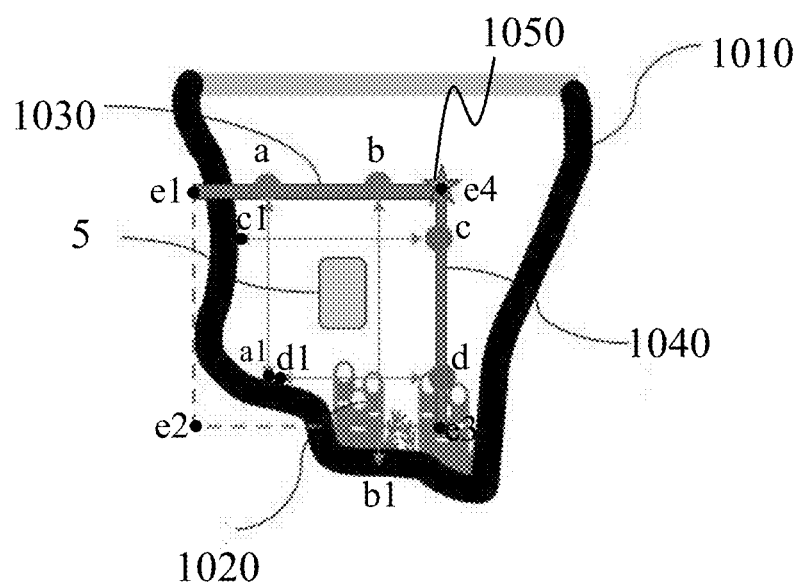
FIG. 10 is a schematic diagram illustrating a structure of a monitoring device disposed in a hot thaw lake pond according to some embodiments of the present disclosure.

Merely by way of example, in a schematic diagram of a structure of the monitoring device disposed in the hot thaw lake pond as illustrated in FIG. 10, 1010 represents a curve of a direction of an underwater terrain; 1020 represents a weed and an impurity on the bottom portion of the water; a line segment e1e4 referred to by 1030 represents an action range of the second lateral electric push rod 501; the line segment e3e4 referred to by 1040 represents an action range of the second vertical electric push rod 503; the rectangular region e1e2e3e4 formed by the action ranges of the second lateral electric push rod 501 and the second vertical electric push rod 503 represents a theoretically accessible region of the monitoring mechanism 5; a pentagram 1050 represents an initial position of the monitoring mechanism 5; a length of a line segment aa1 represents a corresponding depth of the water bottom when the monitoring device is at point a; a length of a line segment bb1 represents a corresponding depth of the water bottom when the monitoring device is at point b; a width of a line segment cc1 represents a horizontally moveable distance of the monitoring device when the monitoring device is at point c; and a width of a line segment dd1 represents a horizontally moveable distance of the monitoring device when the monitoring device is at point d; and then the depth sequence 910-2 may include a length of line segment aa1 and a length of line segment bb1, and the width sequence 910-3 may include the width of line segment cc1 and the width of line segment dd1.

In some embodiments, the depth sequence 910-2 and the width sequence 910-3 may be obtained by the underwater ranging sensor. For example, the underwater ranging sensor may measure the depths of the water bottom corresponding to the plurality of different horizontal position points of the monitoring device at the initial position and a position near the initial position, to form the depth sequence 910-2.

As another example, the underwater ranging sensor may measure horizontally moveable distances corresponding to a plurality of position points of the monitoring device with different water depths at an initial position and the position near the initial position, to form the width sequence 910-3.

The initial position refers to a position where both the second lateral electric push rod and the second vertical electric push rod are at the origin. The origin refers to a position point where the second lateral electric push rod is not pushed out laterally and the second vertical electric push rod is not pushed out vertically.

The position near the initial position may be a region within a present radius centered on the initial position. The present radius may be present by the person skilled in the art based on experience. In some embodiments, the remote terminal may randomly select a plurality of different horizontal position points and a plurality of position points with different water depths.

In some embodiments, the ranging sensor may also send the obtained depth sequence 910-2 and width sequence 910-3 to the communication module and then send the depth sequence 910-2 and width sequence 910-3 to the remote terminal that receives the monitoring data obtained by the monitoring device.

The image data sequence refers to a sequence of a plurality of underwater images taken from different positions. The image data sequence may reflect the topographic orientation, weed condition, impurity condition, etc. underwater of the monitoring waters. The weed condition may include weed distribution, weed quantity, etc. The impurity condition may include impurity distribution, impurity quantity, etc.

In some embodiments, the image data sequence may be obtained by an underwater camera device (e.g., a video camera). In some embodiments, the underwater camera device may also send the obtained image data sequence to the communication module, which then sends the image data sequence to the remote terminal that receives the monitoring data obtained by the monitoring device.

The remote terminal refers to a terminal that generates commands to control the movement of the regulating lever. For example, the remote terminal may include a mobile terminal (e.g., a cell phone, etc.), a computer, a wearable device, etc.

In some embodiments, the remote terminal may send generated commands for controlling the movement of the regulating lever to the communication module, and the communication module receives the commands and sends them to the controller.

The control commands may be configured to control the movement of the regulating lever. The movement of the regulating lever may include movement of the regulating lever and/or rotation of the regulating lever. The movement of the regulating lever may drive the monitoring mechanism to a corresponding monitoring position. The movement of the regulating lever may be realized by the opening or closing of the motor that controls the movement of the regulating lever. The rotation of the regulating lever may be realized by controlling a rotational speed of the motor that controls the rotation of the regulating lever. Descriptions regarding the monitoring position may be found hereinafter.

In some embodiments, a user may operate the remote terminal autonomously, and send the control command to the communication module through the remote terminal. Then, the communication module sends the control command to the controller, and the controller, based on the control command, controls the work of the corresponding motor controlling the movement of the regulating lever and/or controls the rotational speed of the corresponding motor controlling the rotation of the regulating lever, so as to realize remote manual control of the movement of the regulating lever. In some embodiments, the autonomous operation of the user on the remote terminal may include one or more of the text input, voice input, touch operation, slide operation, etc.

For example, if the monitoring device is set up with one regulating lever corresponds to one motor controlling the movement of the regulating lever or one motor controlling the rotation of the regulating lever, the user may autonomously operate the remote terminal to send the control command to the communication module, and the communication module then sends the control command to the controller. The controller may control, based on the control command, the opening or closing of each corresponding motor controlling the movement of the regulating lever, and/or the rotational speed of the motor controlling the rotation of the regulating lever, to control the movement of each regulating lever.

In some embodiments, the remote terminal may also process, based on the monitoring data obtained by the monitoring device, to automatically determine the control command. Detailed descriptions regarding processing the monitoring data obtained by the monitoring device to automatically determine the control command may be found hereinafter.

In some embodiments of the present disclosure, through the setting of the communication module, the controller, and the remote terminal, not only may the user control the remote terminal by manipulating the remote terminal to send the control command to the controller, and remotely control the movement of the regulating lever by the controller, but also may the remote terminal receive the monitoring data obtained by the monitoring device, process the monitoring data to automatically determine the control command, send the control command to the controller, and then control the movement of the regulating lever through the controller to meet different users' needs.

In some embodiments, the control command may include a command for sequentially adjusting the monitoring mechanism to a plurality of monitoring positions.

The monitoring position refers to a location where the monitoring mechanism detects the methane gas in the monitoring waters.

In some embodiments, the remote terminal may determine a plurality of the monitoring positions based on the environmental data, via the first predictive model. Descriptions regarding the environmental data may be found hereinabove.

In some embodiments, the first predictive model may be located at the remote terminal. In some embodiments, the first predictive model is a machine learning model. In some embodiments, the type of the first predictive model may include Neural Network (NN) models and Convolutional Neural Network (CNN) models.

Figure 9:
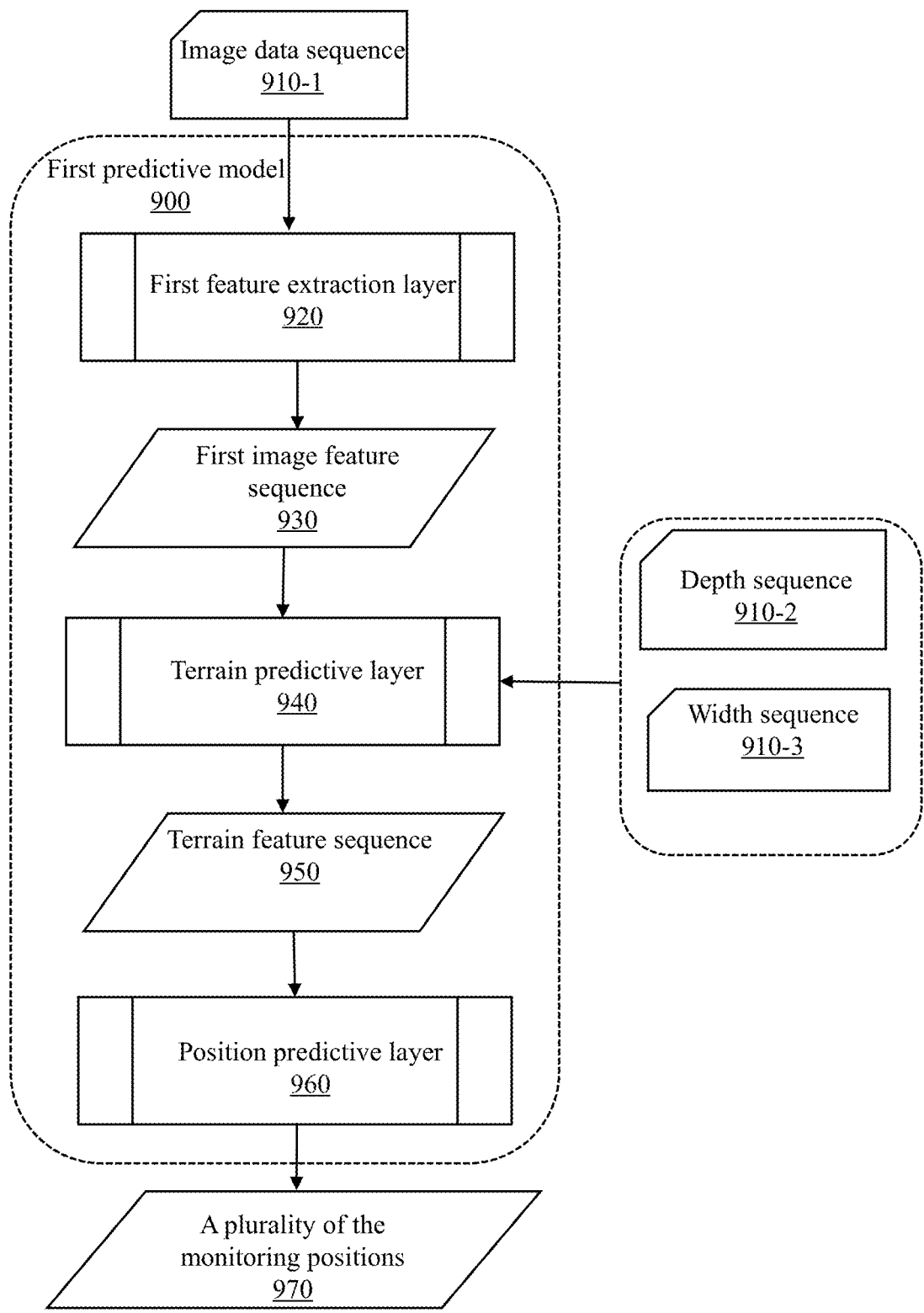
FIG. 9 is a schematic diagram illustrating a structure of a first predictive model according to some embodiments of the present disclosure.

FIG. 9 is a schematic diagram illustrating a structure of a first predictive model according to some embodiments of the present disclosure.

In some embodiments, a first predictive model 900 may include a first feature extraction layer 920, a terrain predictive layer 940, and a position predictive layer 960. The first feature extraction layer 920 may be a CNN. The terrain predictive layer 940 and the position predictive layer 960 may be a NN.

In some embodiments, the first feature extraction layer 920 may be configured to process image data sequence 910-1 to determine a first image feature sequence 930.

The first image feature sequence 930 refers to a sequence including a plurality of first image features. The first image feature refers to a feature extracted from the image data sequence 910-1 and relates to the underwater terrain of the monitoring waters. The first image feature sequence 930 may reflect an overall direction, an overall shape, etc. of the underwater terrain of the monitoring waters.

In some embodiments, the terrain predictive layer 940 may be configured to process the depth sequence 910-2, the width sequence 910-3, and the first image feature sequence 930 output by the first feature extraction layer 920 to determine the terrain feature sequence 950.

In some embodiments, the terrain feature sequence 950 refers to a sequence including a plurality of underwater ground coordinates. The plurality of underwater ground coordinates may be a plurality of underwater ground coordinates randomly selected within a rectangular region including action ranges of the second lateral electric push rod 501 and the second vertical electric push rod 503.

A two-dimensional coordinate system of an underwater ground profile may be constructed by taking an initial position 1050 in FIG. 10 as the origin, the action range of the second lateral electric push rod in FIG. 10 as the x-axis, and action range of the second vertical electric push rod in FIG. 10 as the y-axis.

The randomly selected plurality of underwater ground coordinates may be located within a rectangular region formed by the action ranges of the second lateral electric push rod and the second vertical electric push rod. For example, as shown in FIG. 10, the randomly selected plurality of underwater ground coordinates may include coordinates of any present count of points on the curve 1010 of the direction of the underwater terrain within the rectangular region e1e2e3e4. The present count may be present by a person skilled in the art based on experience.

In some embodiments, the first feature extraction layer 920 and the terrain predictive layer 940 may be obtained by joint training based on a plurality of first training samples with first labels.

The first training sample may include an image data sequence, a depth sequence 910-2, and a width sequence 910-3 of a historical sample hot thaw lake pond, and the first labels may be a terrain feature sequence of the historical sample corresponding to the first training sample.

The first training sample may be obtained based on historical environmental data. The first label of the first training sample may be obtained by predicting based on the historical environmental data. The first label of the first training sample may also be obtained by obtaining the underwater terrain corresponding to the first training sample in a present manner and transforming it into coordinate data. The present manner may include a depth sounder, high and clear water underwater photography, a human survey, etc.

In some embodiments, the remote terminal may input the image data sequence of the historical sample hot thaw lake pond in the first training sample with the first label into an initial first feature extraction layer, and then a depth sequence 910-2 and a width sequence 910-3 of the historical sample hot thaw lake pond, and the first image feature sequence output from the initial first feature extraction layer into the initial terrain predictive layer. The loss function is constructed from predictive results of the first label and the initial terrain predictive layer, and parameters of the initial first feature extraction layer and the initial terrain predictive layer are iteratively updated based on the loss function. Until the loss function converges, a count of iterations reaches the threshold, etc., the training is completed, and a trained first feature extraction layer and a trained terrain predictive layer are obtained.

In some embodiments, the position predictive layer 960 may be configured to process the terrain feature sequence 950 output by the terrain predictive layer 940 to determine a plurality of the monitoring positions 970. Each of the plurality of monitoring positions may be represented in the form of two-dimensional coordinates. The two-dimensional coordinates may be two-dimensional coordinates obtained based on the underwater ground coordinate system as illustrated previously.

In some embodiments, the position predictive layer 960 may be trained based on a plurality of second training samples with second labels.

The second training sample may include the terrain feature sequence of a historical sample hot thaw lake pond, and the second label may be a plurality of historical sample monitoring positions corresponding to the plurality of second training samples.

The second training sample may be obtained based on historical data. The second label of the second training sample may be obtained based on manual labeling. A specific count of the manually labeled monitoring positions for the historical samples may be determined by the person skilled in the art in conjunction with the monitoring device, in the actual terrain, within a reachable range. For example, the person skilled in the art may select any plurality of locations uniformly distributed within the reachable range of the monitoring device in the actual terrain, as the historical sample monitoring positions.

In some embodiments, after determining the plurality of the monitoring positions, the remote terminal may also determine, based on the plurality of the monitoring positions, a corresponding moving order, and corresponding moving directions and moving distances of the second lateral electric push rod and the second vertical electric push rod for each movement, thereby generating a corresponding control command. The moving order may be realized in a plurality of ways. For example, the remote terminal may determine the moving order based on a plurality of the monitoring positions determined according to the distance of the monitoring positions to the water surface. For example, the moving order corresponding to the plurality of the monitoring positions may be determined by a sequence from the closest to furthest distance of the monitoring positions to the water surface.

In some embodiments of the present disclosure, when the underwater topography is not clear, the reachable range of the monitoring mechanism is determined by predicting the underwater topography. Then, within the reachable range, the plurality of the monitoring positions are automatically determined for monitoring the methane gas, thereby avoiding collisions between the monitoring mechanism and the water bottom caused by blindly switching of the monitoring positions, which may lead to damage to the monitoring device.

At the same time, the monitoring efficiency may be improved by automatically determining a reasonable monitoring position, and then automatically arriving at the monitoring position according to the sequence of the control commands for monitoring methane gas.

In some embodiments, the control commands may also include commands for controlling the rotational speed of the motor in the monitoring mechanism 5.

In some embodiments, the rotational speed of the motor is determined based on a first rotational speed and a second rotational speed.

In some embodiments, the remote terminal may take the one with the larger value of the first rotational speed and the second rotational speed as the speed at which the motor rotates, i.e., the speed at which the motor rotates=max {first rotational speed, second rotational speed}.

In some embodiments, the remote terminal may also take a value determined after weighted averaging the first rotational speed and the second rotational speed as a speed at which the motor rotates, i.e., speed at which the motor rotates=a*first rotational speed+b*second rotational speed, wherein $0 \leq a \leq b \leq 1$, a+b=1. The specific values of a and b may be determined by a person skilled in the art according to the actual situation. The weight of the second rotational speed is set to be greater than the weight of the first rotational speed, representing that more weight is placed on the ability of the monitoring device to separate the methane concentration than on the weeding ability of the monitoring device.

The first rotational speed refers to a rotational speed determined based on the weed and/or impurity conditions of a position near a target monitoring location.

The target monitoring location is the location where the methane gas concentration is being monitored this time. The target monitoring location may correspond to a methane concentration sequence as well as a weed and/or impurity characteristic of the position near the target monitoring location. The weed and/or impurity characteristic may include weed and/or impurity distribution, weed and/or impurity count, etc.

The position near the target monitoring location refers to a region within a preset monitoring radius centered on the target monitoring location. The preset monitoring radius may be preset by a person skilled in the art based on experience.

In some embodiments, the first rotational speed may be related to the target monitoring location and the image data sequence.

In some embodiments, the remote terminal may determine the first rotational speed based on the target monitoring location and the image data sequence via a second predictive model.

In some embodiments, the second predictive model is a machine learning model. In some embodiments, the type of the second predictive model may include Neural Network (NN) models and Convolutional Neural Network (CNN) models.

In some embodiments, the second predictive model may include a second feature extraction layer and a first predictive layer. The second feature extraction layer may be a CNN. The first predictive layer may be an NN.

In some embodiments, the second feature extraction layer may be configured to process the image data sequence and the target monitoring location to determine a second image feature sequence.

The second image feature sequence refers to a sequence including a plurality of second image features. The second image features refer to features extracted from the image data sequence that relates to weed or impurity in the position near the target monitoring location. The second image feature sequence may reflect the weed and/or impurity distribution, the count of weeds and/or impurities, etc., of the position near the target monitoring location.

In some embodiments, the first predictive layer may be configured to process the second image feature sequence output from the second feature extraction layer to determine the first rotational speed.

In some embodiments, the second predictive model may be obtained by joint training based on a plurality of third training samples with third labels.

The third training sample may include an image data sequence of a historical sample hot thaw lake pond and a target monitoring location, and the third label may be a first rotational speed of the historical sample corresponding to the third training sample.

The third training sample and the third training label may be obtained based on the historical data. Specifically, since the image data sequence of the historical sample hot thaw lake pond and the historical sample first rotational speed in the historical data are in a one-to-one relationship, the image data sequence of the historical sample in which the weeding effect meets preset requirements and the historical sample first rotational speed, respectively, as the third training sample and the third label.

Because weeds in the water affect the amount of liquid that enters the mounting cylinder, the remote terminal may measure the weeding effect by determining whether or not the time spent reaches the preset time when the amount of liquid that enters the mounting cylinder reaches the preset requirements. For example, the faster the time, the better the weeding effect. The preset requirements and the preset time may be preset by a person skilled in the art based on experience.

In some embodiments, the remote terminal may input the image data sequence of the historical sample hot thaw lake pond from the third training sample with the third label into the initial second feature extraction layer. The second image feature sequence output from the initial second feature extraction layer is then input into the initial first predictive layer, and a loss function is constructed from the third label and predictive results of the initial first predictive layer. Parameters of the initial second feature extraction layer and the initial first predictive layer are iteratively updated based on the loss function. Until the loss function converges, a count of iterations reaches a threshold, etc., the training is completed, and a trained second predictive model is obtained.

The second rotational speed refers to a rotational speed determined based on the methane concentration sequence at the target monitoring location.

In some embodiments, the second rotational speed may be related to the methane concentration sequence at the target monitoring location.

Because of the similarity of methane concentrations at the target monitoring location and the position near the target monitoring location, the methane concentration at the target monitoring location may be represented by the sequence of methane concentration at a previous monitoring position near the target monitoring location. In some embodiments, the methane concentration sequence at the target monitoring location may be a sequence including methane concentrations at a plurality of other positions near the target monitoring location that were monitored before the current monitoring position.

In some embodiments, the remote terminal may obtain the methane concentration at the target monitoring location based on historical data.

In some embodiments, the remote terminal may determine the second rotational speed based on the methane concentration sequence at the target monitoring location via a third predictive model.

In some embodiments, the third predictive model is the machine learning model. In some embodiments, the type of the third predictive model may include Neural Network (NN) models and Convolutional Neural Network (CNN) models.

In some embodiments, the third predictive model may be trained based on a plurality of fourth training samples with fourth labels.

The fourth training sample may include a methane concentration sequence at a target monitoring location of a historical sample hot thaw lake pond, and the fourth label may be a second rotational speed of the historical sample corresponding to the fourth training sample.

The fourth training sample may be obtained based on historical data. In some embodiments, since a set of the methane concentration sequence corresponds to a target monitoring location of the historical sample hot thaw lake pond, a plurality of water extraction and separation experiments on the methane gas may be performed at the same historical sample hot thaw lake pond monitoring position. In this case, a different second rotational speed of the historical sample is used for each experiment, the methane concentration of each experiment is compared, and the second rotational speed of the historical sample with the highest methane concentration is designated as the fourth label. The highest methane concentration represents the most complete separation of methane from the water, and the methane concentration obtained is the closest to a real value of the methane concentration in the hot thaw lake pond.

In some embodiments of the present disclosure, in determining a command for the rotational speed of the motor in the monitoring mechanism, the effects of the methane concentration at the target monitoring location and the weeds are considered in combination, which may ensure that methane in the water is sufficiently separated to improve the final accuracy of the methane concentration obtained by monitoring. Moreover, the demand for weed removal may also be satisfied, so that the amount of liquid entering the mounting cylinder quickly reaches the requirement, which improves the efficiency of obtaining the methane concentration by monitoring.

In addition, for the same target monitoring location in the same set of training samples, it is possible to perform a plurality of fetch tests with different rotational speeds for each experiment, so as to obtain the rotational speed with a best methane separation effect based on the same methane feature sequence. However, at the same target monitoring location, the weeds are gone or reduced after being cut once and are not reproducible, the actual image data sequence is not the same under such a plurality of tests even though the target monitoring location is the same. In this case, it is not possible to determine the rotational speed with the best weeding effect when the image data sequence is the same. Therefore, by designating the image data sequence and the methane concentration sequence at the target monitoring location as different model inputs and training them separately, it is possible to improve the accuracy of the predictive results of the second predictive model and the third predictive model obtained by the final training.

Obviously, the described embodiments are only a portion of the embodiments in the present disclosure and not all of the embodiments. Based on the embodiments in the present disclosure, all other embodiments obtained by a person of ordinary skill in the art and in the related field without creative labor may fall within the scope of protection of the present disclosure. Structures, apparatuses, and methods of operation not specifically described and limited in the present disclosure are implemented according to the conventional means in the field if not otherwise specified and limited.

At the same time, the disclosure uses specific words to describe embodiments of the disclosure. For example, "an embodiment", "one embodiment", and/or "some embodiments" means a feature, structure, or characteristic associated with at least one embodiment of the present disclosure. Therefore, it is emphasized and should be appreciated that two or more references to "an embodiment" or "one embodiment" or "an alternative embodiment" in various portions of the present disclosure are not necessarily all referring to the same embodiment. In addition, some features, structures, or characteristics of one or more embodiments in the present disclosure may be properly combined.

Furthermore, the recited order of processing elements or sequences, or the use of numbers, letters, or other designations therefore, is not intended to limit the claimed processes and methods to any order except as may be specified in the claims. Although the above disclosure discusses some embodiments of the invention currently considered useful by various examples, it should be understood that such details are for illustrative purposes only, and the additional claims are not limited to the disclosed embodiments. Instead, the claims are intended to cover all combinations of corrections and equivalents consistent with the substance and scope of the embodiments of the invention. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that object of the present disclosure requires more features than the features mentioned in the claims. Rather, claimed subject matter may lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes. History application documents that are inconsistent or conflictive with the contents of the present disclosure are excluded, as well as documents (currently or subsequently appended to the present specification) limiting the broadest scope of the claims of the present disclosure. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A monitoring device for methane gas in a hot thaw lake pond in a tundra region, comprising: a top plate, an adjusting mechanism, and a monitoring mechanism; wherein a bottom portion of the top plate is fixedly connected with a fixed column, the adjusting mechanism is slidably mounted on the fixed column, and the adjusting mechanism moves up and down along the fixed column to adjust a position of the adjusting mechanism;

the monitoring mechanism is connected to the adjusting mechanism, and the monitoring mechanism controls entry and exit of water to be monitored and detects methane gas in the water;

the monitoring mechanism includes a second lateral electric push rod, a slide seat, a second vertical electric push rod, a mounting cylinder, and a sealing base plate; wherein the slide seat is slidably mounted in a lateral chute of the adjusting mechanism, and the slide seat is connected with an action end of the second lateral electric push rod; and a top end of the second vertical electric push rod is fixed to the slide seat, and the mounting cylinder is fixedly connected to a bottom end of the second vertical electric push rod;

a motor box, a first electric telescopic rod, a turntable, a second electric telescopic rod, and a methane detection sensor are provided in the mounting cylinder, wherein the motor box is fixed on a top of the mounting cylinder, a motor is provided in the motor box, an output shaft of the motor is connected with the first electric telescopic rod, an action end of the first electric telescopic rod is connected to the turntable, the turntable is slidably mounted in the mounting cylinder; and the first electric telescopic rod drives the turntable to slide up and down along the mounting cylinder, the motor drives the turntable to rotate through the first electric telescopic rod, and the turntable has a plurality of stirring heads on a bottom plane of the turntable;

the second electric telescopic rod is connected to a bottom portion of the turntable, an action end of the second electric telescopic rod is connected to the sealing base plate to drive the sealing base plate to move up and down to realize opening and closing of the sealing base plate and a lower port of the mounting cylinder; and a debris removal mechanism is provided on the monitoring mechanism, the debris removal mechanism includes a rotation ring rotationally sheathed to the mounting cylinder, snap rings are provided on upper and lower sides of the rotation ring; the rotation ring is connected to the sealing base plate by a telescopic connecting plate, a cleaning plate is connected to the rotating ring, a cutting edge is provided on an outer wall of the cleaning plate, and curved guide plates are provided on both sides of the cleaning plate.

2. The monitoring device of claim 1, wherein the adjusting mechanism includes an articulating ring, the articulating ring is slidably sheathed to the fixed column, a support arm is fixedly connected to an outer wall of the articulating ring, and the support arm is configured to mount the monitoring mechanism; and a post is provided on the articulating ring along a radial direction of the articulating ring, and a plurality of holes are provided on the fixed column, and adjustment and positioning of the articulating ring along an up and down position of the fixed column is realized by adjusting the post to fit different holes.

3. The monitoring device of claim 1, wherein a base is fixedly connected to a bottom of the fixed column.

4. The monitoring device of claim 1, wherein an air supply mechanism is provided at the bottom portion of the top plate, the air supply mechanism includes a first lateral electric push rod, a slider, a first vertical electric telescopic rod, an air supply box, a first air outlet pipe, and a second air outlet pipe; and the slider is slidably mounted in a slide groove of the top plate, the slider is connected to an action end of the first lateral electric push rod, a top of the first vertical electric telescopic rod is fixedly connected to the slider, an action end of the first vertical electric telescopic rod is connected to the air supply box, and the first air outlet pipe and the second air outlet pipe are connected to an air outlet of the air supply box, wherein the first air outlet pipe is a vertical pipe for delivering air to the monitoring mechanism, and the second air outlet pipe is a curved pipe for delivering air to an outer surface of the fixed column.

5. The monitoring device of claim 1, wherein the cleaning plate extends downward from the rotation ring and is inclined outwardly.

6. The monitoring device of claim 5, wherein a gap between each position on each of the curved guide plates that is passed through in sequence and a wall of the mounting cylinder is progressively decreasing from a side of each of the curved guide plates connected to the cleaning plate to another side of each of the curved guide plates.

7. The monitoring device of claim 1, wherein a motorized cutting device is provided at a bottom end of the cleaning plate.

8. The monitoring device of claim 1, wherein an air supply mechanism is provided at the bottom portion of the top plate, the air supply mechanism including a first lateral electric push rod and a first vertical electric telescopic rod, and the monitoring device further including a communication module and a controller; wherein the communication module is configured to send monitoring data obtained by the monitoring device to a remote terminal and to receive control commands sent by the remote terminal, the control commands are configured to control movement of a regulating lever, and the regulating lever includes at least one of the first lateral electric push rod, the first vertical electric telescopic rod, the second lateral electric push rod, the second vertical electric push rod, the first electric telescopic rod, and the second electric telescopic rod, and the monitoring data includes methane concentration data or environmental data;

the controller is configured to control the regulating lever based on the control commands transmitted by the communication module; and the communication module and the controller are disposed on the top plate, the communication module being electrically connected to the motor of the regulating lever.

9. The monitoring device of claim 8, wherein the control commands include commands for sequentially adjusting the monitoring mechanism to a plurality of monitoring positions, the plurality of monitoring positions are determined based on the environmental data by a first predictive model, the environmental data includes a depth sequence, a width sequence, and an image data sequence, the first predictive model is located at the remote terminal, and the first predictive model is a machine learning model.

10. The monitoring device of claim 8, wherein the control commands include commands for controlling a rotational speed of the motor in the monitoring mechanism, the rotational speed of the motor is determined based on a first rotational speed and a second rotational speed, the first rotational speed is related to a target monitoring location and an image data sequence, and the second rotational speed is related to a methane concentration sequence at the target monitoring location.

* * * * *